United States Patent [19]
Grossman et al.

[11] Patent Number: 5,910,440
[45] Date of Patent: Jun. 8, 1999

[54] METHOD FOR THE REMOVAL OF ORGANIC SULFUR FROM CARBONACEOUS MATERIALS

[75] Inventors: Matthew J. Grossman, Flemington; Michael Siskin, Randolph; David T. Ferrughelli, Flemington; M. Kathryn Lee, Plainfield, all of N.J.; James D. Senius, Seabrook, Tex.

[73] Assignee: Exxon Research and Engineering Company, Florham Park, N.J.

[21] Appl. No.: 08/632,040

[22] Filed: Apr. 12, 1996

[51] Int. Cl.⁶ .............................. A01N 63/00; C02F 3/00; C10G 32/00; C12N 1/00
[52] U.S. Cl. .................... 435/282; 424/93.4; 435/252.1; 435/822; 435/262.5; 210/601; 210/606
[58] Field of Search .................................. 435/282, 822, 435/262.5, 252.1; 424/93.4; 210/601, 606

[56] References Cited

U.S. PATENT DOCUMENTS

| | | | |
|---|---|---|---|
| 3,884,797 | 5/1975 | Alley, Jr. et al. | 208/89 |
| 4,331,639 | 5/1982 | Hass et al. | 423/235 |
| 4,465,493 | 8/1984 | Attar | 44/15 R |
| 5,002,888 | 3/1991 | Kilbane, II | 435/252.31 |
| 5,034,204 | 7/1991 | Moser et al. | 423/243 |
| 5,607,857 | 3/1997 | Grossman et al. | 435/282 |

*Primary Examiner*—David M. Naff
*Assistant Examiner*—Deborah K. Ware
*Attorney, Agent, or Firm*—Ronald D. Hantman

[57] ABSTRACT

A process to remove organic sulfur from organic compounds and organic carbonaceous fuel substrates containing sulfur compounds having sulfur-carbon bonds is disclosed. The steps of the process include oxidizing the sulfur species to the sulfone and/or sulfoxide form, and reacting the sulfone and/or sulfoxide form in an aqueous media of the reacting step including a hydride transfer reducing agent. In a particular embodiment, the reducing agent is sodium formate, the oxidizing agent is a microorganism as exemplified by Rhodococcus species ATCC 55309 or Rhodococcus species ATCC 55310 or combinations thereof.

15 Claims, No Drawings

METHOD FOR THE REMOVAL OF ORGANIC SULFUR FROM CARBONACEOUS MATERIALS

BACKGROUND OF THE INVENTION

The present invention relates to the removal of sulfur from carbonaceous materials, fuels, and fuel precursors (resources). The combustion of sulfur compounds in carbonaceous fuels produces pollutants in the form of acidic sulfur oxide gaseous emissions. Concern about the environmental impact of these pollutants has resulted in stricter regulations on allowable sulfur levels in fuels. The requirement for lower sulfur levels and the increased reliance on heavier high sulfur feedstocks will require increased refinery desulfurization capacity. Further, to achieve low fuel sulfur levels requires the removal of those compounds that resist conventional hydrodesulfurization, notably the sterically hindered dibenzothiophene compounds. Limitations on the ability of conventional hydrodesulfurization to remove these compounds, and the high cost of hydrogen, place great emphasis on the development of novel desulfurization technology.

Fossil fuels contain significant quantities of sulfur, largely in the form of organic sulfur containing molecules. Sulfur in fuels causes corrosion of transportation and processing equipment, fouling of processing catalysts and upon combustion, air pollution in the form of acidic gas emissions. The sulfur content of hydrocarbon feeds entering refineries has increased steadily over the last ten years exacerbating sulfur related problems. In the United States and abroad environmental concerns about sulfur related air pollution have resulted in more stringent regulations on the sulfur content of fuels. High sulfur refinery feeds combined with more stringent regulations place a great emphasis on the development of new methods to reach extremely low fuel sulfur levels.

SUMMARY OF THE INVENTION

The present invention is a process to remove organic sulfur from organic compounds and organic carbonaceous fuel substrates containing sulfur compounds having sulfur-carbon bonds. The steps of the process include oxidizing the sulfur species to the sulfone and/or sulfoxide form, and reacting the sulfone and/or sulfoxide form in an aqueous media. The aqueous media of the reacting step includes a hydride transfer reducing agent. In a particular embodiment, the reducing agent is sodium formate.

In a preferred embodiment, the oxidizing step is performed using a biocatalyst. A biocatalyst is defined as any organism or fraction of an organism (e.g., cell fraction, cell extract, crude or purified enzyme preparation) capable of performing the desired reaction. In a particular embodiment, the biocatalyst is microorganisms selected from the group which is capable of a selective oxidation of the sulfur in organic sulfur compounds, to the sulfoxide and/or sulfone form, without concomitant oxidation of other components of the molecule. In a particular embodiment, the reducing agent is sodium formate, the microorganism is Rhodococcus species ATCC 55309 or Rhodococcus species ATCC 55310 or combinations thereof.

DESCRIPTION OF THE PREFERRED EMBODIMENT

In standard refinery operations organic sulfur in fuels is removed by hydrodesulfurization requiring heterogeneous inorganic catalysts, high temperature and high hydrogen gas pressure. These methods are effective in removing thiols, most sulfides and disulfides, but are less effective against thiophenic sulfur, particularly the dibenzothiophenes containing substitutions rendering the sulfur atom sterically hindered, i.e., monobeta- and dibeta-substituted dibenzothiophenes. Tighter regulations on the amount of sulfur allowable in fuels will necessitate the removal of sulfur from even the most recalcitrant sulfur compounds. To achieve low sulfur levels requires the processing of fuels under much more severe conditions, i.e., increased temperature and hydrogen pressure, thereby greatly increasing the cost of fuel processing (e.g., thicker walled reactors, higher hydrogen consumption/costs). The cost and limitations of conventional desulfurization places great emphasis on the development of new technologies to meet developing needs.

Aqueous based systems can catalyze the desulfurization of organic sulfur molecules at elevated temperatures, in the range of 400° C., without molecular hydrogen (Energy Fuels 1995, 9, 331). The removal of sulfur is greatly enhanced when the sulfur is oxidized to the sulfoxide form and further enhanced if the sulfur is oxidized to the sulfone. Therefore, oxidation of the sulfur moiety activates these compounds to subsequent desulfurization by aqueous based reagents. The selective chemical oxidation of organic sulfur in whole fuels is possible, but can be problematic. Oxidation with strong oxidizing agents will result in the unwanted oxidation of hydrocarbons. Oxidation with peroxide oxidants is more selective for sulfur but is impractical for use with hydrocarbonaceous fuels due to the potential formation of explosive hydroperoxides and endoperoxides. The use of peracids is another selective, albeit uneconomical, method of oxidation to sulfoxides and/or sulfones. Extraction of the sulfur components followed by oxidation adds another step, but may increase the viability of many of these oxidizing reagents.

There are several methods for the selective oxidation of the organic sulfur compounds.

Biocatalytic sulfur selective oxidation provides a safe and efficient method to activate organic sulfur compounds for subsequent desulfurization using aqueous based chemistry. Preferred organisms for the selective oxidation of organic sulfur compounds in fuel are selected from the group of organisms consisting of Rhodococcus species ATCC 55309 and 55310. The culture have been deposited with the American type culture collection, 12301 Park Lawn Drive, Rockville, Md. 20852 and assigned ATCC numbers 55309 and 55310. These organisms selectively oxidize sulfur compounds, including the sterically hindered dibenzothiophenes, to the corresponding sulfoxides and sulfones.

This invention combines a biological method for selective partial oxidation of organic sulfur compounds to the corresponding sulfoxides and sulfones, with a subsequent chemical step to complete desulfurization that does not require diatomic hydrogen. Biological desulfurization processes that remove organic sulfur by complete oxidation to sulfite or sulfate require two to three moles of diatomic oxygen per mole of sulfur removed and a series of enzymatic steps which can also lead to loss of organic carbon and associated fuel value. Partial oxidation to sulfoxides and sulfones significantly reduces oxygen demand and simplifies the biological system while providing a selective method to activate sulfur compounds in fuels for subsequent chemical desulfurization. Table 1 illustrates examples of enzymatic oxidation of organic sulfur compounds for subsequent aqueous based desulfurization. Table 2 illustrates examples of aqueous based desulfurization of oxidized sulfur compounds.

In the preferred embodiment, the oxidation of the sulfur in organic sulfur compounds and species in the fuel is performed at mild temperatures (0–100° C.), in the presence of oxygen, by contacting the fuel with a biocatalyst. The biocatalyst being selected from the group of microorganisms which are capable of a selective oxidation of the sulfur in the organic sulfur species, to the sulfoxide and/or sulfone form, without concomitant oxidation of other components of the molecule or macromolecule. In a further preferred embodiment, the gene(s) encoding the enzyme(s) responsible for the selective oxidation of sulfur, are cloned, from the organism originally possessing these genes, into a recipient organism (e.g., *Esherichia coli*, or other suitable host cell line, including the original cell line) under the control of a genetic promoter which allows production of the enzyme(s) at levels which enhance the amount of active enzyme. Techniques for cloning these genes are well known in the art, and are described in Maniatis, T., et al, (1989) Molecular Cloning: a Laboratory Manual, 2d ed., Cold Spring Harbor Laboratory Press, and Current Protocols in Molecular Biology, Ausubel, F. M., et al, eds., Sarah Greene, pub., New York (1990). In a further preferred embodiment, the enzymes responsible for sulfur oxidation are used directly in the form of free enzymes, enzymes modified with chemical groups to alter their solubility characteristics (e.g., with fatty acids to make them soluble in a hydrocarbon phase to allow more efficient contacting with the hydrocarbon phase), enzymes immobilized in gels (e.g., carageenan, polyacrylamide, agarose and alginate), and enzymes immobilized on solid supports (e.g., diatomaceous earth, glass beads, or ion exchange resions).

Microorganisms known to perform selective sulfur oxidation include Rhodococcus (previously identified as Arthrobacter) strains ATCC 55309 and ATCC 55310 (pending patent application U.S. Pat. No. 5,607,857, issued Mar. 4, 1997), *Rhodococcus rhodochrous* strain ATCC 53968 (U.S. Pat. No. 5,104,801) *Bacillus sphaericus* strain ATCC 53969 (U.S. Pat. No. 5,002,888), *Rhodococcus erythropolis* strains N1-36 and D-1 (Wang, P. and Krawiec, S. (1994) Desulfurization of dibenzothiophene to 2-hydroxybiphenyl by some newly isolated bacterial strains. Arch. Microbiol. 161, 266–271, Izumi, Y., Ohshiro, T., Ogino, H., Hine, Y. and Shimao, M. (1994) Selective desulfurization of dibenzothiophene by *Rhodococcus erythropolis* D-1. Appl. Environ. Microbiol. 60, 223–226), Corynebacterium strain SY1 (Omori, T., Monna, L., Saiki, Y., and Kodama, T. (1992) Desulfurization of dibenzothiophene by Corynebacterium sp. Stain SY1. App. Envir. Micro. 58, 911–915) and Brevibacterium strain DO (van Afferden, M., Schacht, S., Klein, J. and Truper, H. G. (1990) Degradation of dibenzothiophene by Brevibacterium sp. DO. Arch. Microbiol. 153, 324–328).

A. Biocatalytic Oxidation

Current biological desulfurization technologies rely on the use of microorganisms which non-selectively degrade sulfur containing compounds, and concomitantly structurally related non-sulfur compounds, resulting in a significant reduction of the fuel content (fuel value, heating value) in the product. Recently, progress has been made in the discovery of microorganisms which can selectively remove organically bound sulfur in the form of aqueous soluble sulfur waste (sulfate) without degrading the fuel content. Evidence from the study of these sulfur selective systems demonstrates that they require the activity of a number of enzymes operating in concert in a multi-step process. Due to the oxidative nature of the sulfur selective systems two to three moles of $O_2$ are required per mole of sulfur removed. The relatively large amount of oxygen required and the low solubility of oxygen in water make oxygen mass transfer potentially the most important parameter controlling reaction rate and reactor size.

The ability to use the selectivity of biological desulfurization systems with a decreased requirement for oxygen would significantly reduce the limitations imposed by oxygen mass transfer. In addition, the use of a biological system which has the fewest number of steps will facilitate the development of an economic process for biological desulfurization of fuels.

In the preferred embodiment the fuel to be desulfurized is, at mild temperatures (0–100° C.), in the presence of oxygen, brought into contact with the biocatalysts (either whole cell, cell fraction, or enzyme preparation), contained within an aqueous buffer containing mineral salts, and if required a carbon, nitrogen and phosphorous source, and if required cofactors (e.g., NAD(P)H), for a sufficiently long period of time to allow the conversion of all, or part of, the organic sulfur into the corresponding sulfoxides and sulfones. Following oxidation of the sulfur, the treated fuel is separated from the biocatalysts, by any of a variety of standard techniques including gravity separation, gravity separation facilitated by heating, gravity separation facilities by an applied electrical potential (as in crude oil electrostatic desalters), filtration ((1993) Oil and Gas J. 91, 59–60.), and centrifugation. Alternatively, if the biocatalyst is immobilized in a gel or solid support, the fuel may be brought in contact with the biocatalyst and subsequently separated via an outlet port from the reactor without the need for further separation steps. Due to the aqueous nature of the subsequent chemical desulfurization steps, separation of water from the fuel is not required. If water separation is desired, it may be separated by any of the above mentioned techniques. The separated biocatalyst (and water if produced) may be recycled to the reactor for subsequent reuse. Following the separation of the fuel from the biocatalyst, the treated fuel, containing oxidized organic sulfur, is desulfurized by the instant chemical method described herein.

B. Aqueous Based Desulfurization

The process of the present invention is typically carried out at temperatures of from about 200° C. to about 600° C. More preferably temperatures of from about 250° C. to about 550° C., most preferably from about 300° C. to about 500° C. may be used. When a base is not employed in combination with carbon monoxide the carbon monoxide should be introduced into the aqueous system taking care to form and maintain a sufficient concentration of species capable of transferring hydride ions. In the system prior to heating to reaction temperature, CO pressures should be from about 500 psi (3.4 MPa) to about 2,700 psi (18.6 MPa), preferably 700 psi (4.8 MPa) to 1800 psi (12.4 MPa). Equivalent concentrations of formic acid, which thermally decomposes into CO and water, may be used for convenience. Inorganic hydroxide or carbonate base, preferably of Group I and II metals and iron and nickel, more preferably sodium may be added in stoichiometric or excess amounts to form inorganic formate, a preferred hydride ion donor (i.e., a quantitative or stoichiometric amount is based on the amount of CO present). An economical method of carrying out the process would also include adding the inorganic hydroxide or carbonate base in stoichiometric or excess concentration to the formic acid or the hydride ion reducing agent. It is also envisioned that other water stable hydride donor reducing agents, e.g., sodium borohydride, can be used in the present invention. Water unstable hydride donors are acceptable, but feedstocks must be dried prior to reaction. Although the process may be used to effect the decrease in content of S, it is typically more effective in S removal in the presence of base when the sulfur is in the form of a sulfone. It is, therefore, desirable to add an inorganic base as described previously to the aqueous-CO and resource mixture to enhance removal of sulfones. If the sulfur in the S-containing feeds are in the form of sufoxides, it may not be as desirable to add the inorganic base. In mixed sulfone and sulfoxide containing feeds the choice to add optional inorganic base depends largely on the nature of the feed and process economics. Thus, as compared to processes known in the art the process of the present invention may be used to provide enhanced conversion of sulfone and sulfoxide containing structures at the stated CO pressures (concentrations). Organic base may be used in combination with CO to produce the corresponding formate which results in a lower system pressure, and thus may be the economically more preferred route. In order to minimize undesirable side reactions, the process may be carried out using deoxygenated water. The desired reactions typically may be obtained in high yields in as soon as about 5 minutes at reaction conditions. When the reaction time is not of a sufficient duration to produce quantitative reaction the products nevertheless include sulfone and sulfoxide depleted products and other sulfur containing species which can either be reacted for longer times or recycled to the oxidation process species.

Water to starting material ratios of from about 10:1 to 0.5:1 preferably 5:1 to 1:1, more preferably about 2:1 to 1:1 are highly desirable. The operating parameters of temperature, pressure, residence or reaction time and in a continuos system flow velocity, may be balanced within the disclosed ranges to achieve the desired products.

EXAMPLES

Biocatalytic Oxidation

The biocatalytic (enzymatic) oxidation of organosulfur compounds was performed using a recombinant DNA construct of the gene encoding the organic sulfur oxidation enzyme from Arthrobacter sp. ATCC strain 55309, expressed in an *Escherichia coli* host cell line. Products were analyzed by GC/flame-ionization detection/sulfur chemiluminescence detection (GC/FID/SCD) which is able to distinguish between sulfur containing and sulfur free compounds. When authentic standards for a major product was not available products were identified by GC/mass spectroscopy (GC/MS). For GC/FID/SCD analysis, cultures were extracted with decane as an internal injection standard and DBT, or in the case of DBT as test substrate 4,6-diethyldibenzothiophene, as an extraction standard. Samples were analyzed on a Perkin Elmer Autosystem gas chromatograph, equipped with a Sievers Instrument 355B sulfur chemiluminescence detector attached in series to a flame ionization detector, using an SPA-1 column (30 m, 0.24 um id.). The oven temperature program was 40° C. for 1 min., followed by a 4° C./min ramp rate to a final temperature of 300° C., with a final hold for 10 min. For GC/MS analysis, culture extracts and standards were analyzed on an HP 5890 Series II, equipped with a 5757 Mass Selective Detector, using a DB-1 column (30 m, 0.25 um i.d.). Data was collected and analyzed on an HP Chemstation and peak identifications not confirmed by authentic standards were identified by PBS Library Search. The oven temperature program was 100° C. for 5 min., followed by a 5° C./min ramp rate to a final temperature of 310° C., with a final hold for 10 min.

General Procedure for Biocatalytic Oxidation

The gene encoding the organic sulfur oxidation enzyme from Arthrobacter sp. ATCC strain 55309 was inserted into plasmid pQ30 (Qiagen Inc.) such that the gene was expressed from a bacteriophage T5 promoter. Independent cultures of *Escherichia coil* M15 (Qiagen Inc.), transformed with this construct, were prepared in minimal salts medium (pH 7.0), for each compound to be tested. Cultures were grown at 30° C., with shaking at 200 rpm, until cell densities reached an $OD_{600}$ of 0.9. Individual organic sulfur compounds were then added to the cultures to a final concentration of 1 mM. Cultures were then incubated for an additional 72 hr and then extracted with methylene chloride. The methylene chloride extracts were analyzed by GC/FID/SCD, or GC/MS if authentic reaction product standards were not available. Table 1 shows the oxidation products produced by the action of the DBT oxidation enzyme on the organosulfur compounds tested.

The examples in Table 1 show that a broad range of organosulfur chemical types, representative of the majority of compounds present in heavy fractions of crude oils, can be enzymatically oxidized to the sulfoxide and/or the sulfone. Therefore, in combination with the aqueous chemistry claimed herein, sulfur can be removed from the sulfur-containing molecules present in heavy oils, cat cycle oils, residual sulfur in diesel fuels and other petroleum products. The approach is also amenable to sterically hindered condensed thiophene species, as illustrated with 4,6-diethyldibenzothiophene. Sterically hindered compounds, illustrated here by 4,6-diethyldibenzothiophene represent those compounds which are the most resistant to the conventional hydrodesulfurization technology currently employed in the petroleum industry for desulfurization of organic sulfur compounds. Increased reaction time and/or more active biocatalyst would allow for complete oxidation of the sulfur present in the organic sulfur compounds. Increased reaction time and/or more active biocatalyst would allow for complete oxidation of the sulfur present in the organic sulfur compounds.

TABLE 1

| BIOLOGICAL OXIDATION PRODUCTS | |
| --- | --- |
| Test Compound | Major Products |
| Diphenyl Sulfide | Diphenyl sulfide (1.4%) |
| | Diphenyl sulfoxide (39.1%) |
| | Diphenyl sulfone (59.5%) |
| Benzyl Phenyl Sulfide | Benzyl Phenyl Sulfide (3.0%) |
| | Benzyl phenyl sulfoxide (45.4%) |
| | Benzyl phenyl sulfone (24.1%) |
| | Bibenzyl (18.0%) |
| | Diphenyl disulfide (9.5%) |
| Dibenzothiophene | Dibenzothiophene sulfone (100%) |
| 4,6-Diethyldibenzothiophene | 4,6-Diethyldibenzothiophene (77.8%) |
| | 4,6-Diethyldibenzothiophene sulfone (22.2%) |

Biocatalytic Oxidation Followed By Chemical Treatment

The thermolyses and aquathermolyses of these compounds were studied in 15% aqueous $HCO_2H$; and 15% aqueous $HCO_2Na$. Reactions in 15% $HCO_2H$ simulate $CO$—$H_2O$ systems with an initial 900 psi cold charge of CO and 15% aqueous sodium formate simulates $CO$—$H_2O$-base systems.

The 15% aqueous formic acid and 15% aqueous sodium formate solutions were deoxygenated with argon for 1 hour just before use. All the GC analyses were carried out on a Hewlett Packard 5890 gas chromatograph operated in the split injection mode (30:1 ratio) and equipped with a flame-ionization detector (FID). A 30 m capillary column (SPB-5) was used and the oven temperature was programmed from 40° C. to 250° C. with the initial time set at 1 minute and a subsequent rate of 5° C. per minute. The flow rate of the helium carrier gas, hydrogen, and air at room temperature (23° C.) were measured at 29, 39, and 380 mL/minute. GC/MS analyses of all compounds were performed on a Varian 3400 gas chromatograph and a Finnigan MAT 700 ion trap detector.

General Procedure for Aquathermal Reactions

All experiments were carried out in small (0.75 in.) stainless steel Swagelok (plug and cap) bombs which were not equipped for the collection or analysis of gaseous products. The model compound (0.16 g) and deoxygenated aqueous solution (1.14 mL) were charged into the nitrogen-blanketed stainless steel bomb which was then sealed. The reactor was then placed, without agitation, into a Techne fluidized sandbath (Model SBS-4) set at 460° C. using a Techne temperature controller (TC-8D) for a time period indicated at a given temperature (2 minute heat-up time to 460° C.). After the reaction time period, the reaction was immediately quenched by cooling the bomb sequentially with cold air and dry ice, and the bombs were carefully opened while the contents were still solidified (at −78° C.), to minimize loss of material. The reactor was then resealed, allowed to warm to 0° C. and again carefully opened.

The product mixture was transferred to a glass vial, being careful to recover the maximum amount of reaction mixture from the reaction vessel. The reaction vessel was then rinsed in diethyl ether and this organic fraction was combined with the reaction mixture. After warming to room temperature, the reaction mixture was extracted with diethyl ether (2×3 mL) and the ether layers combined in a separate glass vial.

An initial GC analysis was performed on the ether solution prior to addition of internal standard. This procedure helps to determine the choice of standard since it is important that the GC peak for the internal standard does not obscure any of the product peaks. An accurately weighed amount of the internal standard, e.g., heptane (ca. 0.050 g), was then added to the ether solution and the resultant solution was again subjected to GC analysis. From the GC traces obtained the reaction mixture was analyzed in a quantitative fashion and the mass of a particular product would be obtained and its yield determined.

The twelve examples in Table 1 below illustrate the reactivity of sulfoxides and sulfones under aqueous-CO conditions. (Water plus carbon monoxide form an equilibrium with formic acid (HCOOH) under pressure. Formic acid is an intermediate strength organic acid which is also a good hydride ion (H$^-$) donating reducing agent. It is the reducing capability which is responsible for desulfurization. Water plus carbon monoxide plus base (e.g., NaOH) form a formate salt (e.g., sodium formate). Sodium formate is basic in aqueous solution because it is a salt of a strong base and a weak acid. The salt is very stable thermally and unlike the acid form (HCOOH) is present in high concentrations because there is no pressure/temperature equilibrium with carbon monoxide. The formate ion of the salt is the reducing agent. It should be noted that generally sulfoxides undergo higher desulfurization conversion in formic acid than in sodium formate. Sulfones are desulfurized better in aqueous sodium formate.

TABLE 2

| Examples[+] | | t(Min) | Medium | % Conv. | Major Products | Comments |
|---|---|---|---|---|---|---|
| 1 and 2 | diphenyl sulfone (PhSO$_2$Ph) | 60 | 15% HCOOH | 100.0 | PhH (83.9%), PhSH (6.7%), PhSPh (7.0%) | 86% desulfurization |
| | | 60 | 15% HCOONa | 100.0 | PhH (74.9%), PhSH (5.3%), PhSPh (13.9%) | 78% desulfurization |
| 3 and 4 | methyl phenyl sulfone (CH$_3$SO$_2$Ph) | 60 | 15% HCOOH | 95.0 | PhH (29.6%), PhSH (29.4%), PhSPh (34.3%) | |
| | | 7 | 15% HCOONa | 97.4 | PhH (56.8%), PhSH (15.9%), CH$_3$SPh (10.5%), PhSPh (86%) | 61.2% desulfurization increases after 1 hour to 62% |
| 5 and 6 | dibenzothiophene sulfone (DBTSO$_2$) | 60 | 15% HCOOH | 60.5 | PhPh (9.6%), DBT (45.6%) | |
| | | 7 | 15% HCOONa | 79.9 | PhPh (26.5%), DBT (23.7%), 2 PhPhOH (28.2%) | 53% desulfurization, 62% after 1 hour |
| 7 and 8 | 4,6-diethyldibenzo-thiophene sulfone (4,6-DIETDBTSO$_2$) | 7 | 15% HCOONa | 99.1 | 2-Et-2'-HOPhPh (10.1%), 3,3'-DiEtPhPh (60.1%), 2-HO-3,3'DiEtPhPh (10.7%), 4,6-DiEtDBT (4.8%) | 85% desulfurization. 4,6-DiEtDBT is <2% converted. |
| | | 30(at 400° C.) | 15% HCOONa | 74.8 | 3,3'-DiEtPhPh (50.1%), 2-HO-3,3'-DiEtPhPh (13.1%), 4,6-DiEtDBT (4.5%) | |
| 9 and 10 | diphenyl sulfoxide (PhSOPh) | 60 | 15% HCOOH | 100.0 | PhH (91.9%), PhSPh (7.2%) | 92.2% desulfurization (86.2% PhSPh after 7 minutes) |
| | | 7 | 15% HCOONa | 100.0 | PhH (25.6%), PhSH (12.4%), PhSPh (57.4%) | No change after 1 hour |

TABLE 2-continued

| Examples[+] | | t(Min) | Medium | % Conv. | Major Products | Comments |
|---|---|---|---|---|---|---|
| 11 and 12 | methyl phenyl sulfoxide ($CH_3SOPh$) | 60 | 15% HCOOH | 100.0 | PhH (84.8%), $PhCH_3$ (7.9%), $CH_3SPh$ (4.9%), PhSPh (1.1%) | 92.7% desulfurization |
| | | 60 | 15% HCOONa | 100.0 | PhH (10.4%), $PhCH_3$ (11.5%), PhSH (13.8%), $CH_3SPh$ (34.2%), PhSPh (22.7%), PhSSPh (4.9%) | 22.8% desulfurization |

[+]all reactions performed at 460° C. except for noted.
Notes:
PhH = benzene
PhSH = thiophenol (also called phenyl mercaptan)
PhSPh = diphenyl sufide
$CH_3SPh$ = methyl phenyl sulfide
PhPh = biphenyl
DBT = dibenzothiophene
2PhPhOH = 2-hydroxybiphenyl
2-Et-29-HOPhPh = 2-ethyl-29-hydroxybiphenyl
3,3'-DiEtPhPh = 3,3'-diethylbiphenyl
4,6-DiEtDBT = 4,6-diethyldibenzothiophene
$PhCH_3$ = toluene
PhSSPh = diphenyldisulfide The examples in Table 2 above shows that the illustrated phenyl sulfones undergo cleavage and desulfurization at 460° C. to form benzene as the major product most efficiently in 15% aqueous sodium formate, whereas the corresponding sulfoxides are most reactive in 15% aqueous formic acid. Other sulfur-containing products in the reaction mixtures, e.g., diphenyl sulfide and phenyl mercaptan (thiophenol), will react to form more benzene at longer reaction times. Even dibenzothiophene sulfone and its highly hindered 4,6-diethyl derivative undergo 50–85% desulfurization in only 7 minutes, whereas the corresponding unoxidized dibenzothiophenes are essentially unreactive. This gives us the potential to remove sulfur from large sulfur-containing molecules from heavy oils, cat cycle oils, residual sulfur in diesel fuels, etc. The approach is especially amenable to highly hindered condensed thiophene species, as illustrated with 4,6-diethyldibenzothiophene sulfone, which are the most difficult to remove.

What is claimed is:

1. A process to remove organic sulfur from carbonaceous materials, fuels, and fuel precursors containing at least one organic sulfur compound having sulfur-carbon bonds, the steps of the process comprising:
   (a) oxidizing said organic sulfur compound to a chemical compound selected from the group consisting of sulfone compounds and sulfoxide compounds and combinations thereof; and
   (b) reacting chemically said chemical compound in an aqueous medium including a hydride transfer reducing agent to reduce the sulfur in said chemical compound.

2. The process of claim 1 wherein said oxidizing step is performed using a biocatalyst.

3. The process of claim 1 wherein said oxidizing step is performed using a selective chemical reagent.

4. The process of claim 2 wherein said oxidizing step is performed using a microorganism.

5. The process of claim 4 wherein said microorganism is Rhodococcus species ATCC 55309 or Rhodococcus species ATCC 55310 or combinations thereof.

6. The process of claim 1 wherein said chemical compound is selected from the group consisting of diphenyl sulfone, methyl phenyl sulfone, dibenzothiophene sulfone, 4,6-diethyldibenzothiophene, diphenyl sulfoxide, and methyl phenyl sulfoxide.

7. The process of claim 6 wherein said hydride transfer reducing agent is formate ion.

8. The process of claim 7 wherein said formate ion is present in an amount of about 15 wt %.

9. The process of claim 1 wherein reacting said chemical compound is carried out in an aqueous medium including a substance selected from the group consisting of formic acid, Group I metal carbonates and metal hydroxides, Group II metal carbonates and metal hydroxides, iron carbonate, nickel carbonate, iron hydroxide, nickel hydroxide, and combinations thereof.

10. The process of claim 2 wherein said biocatalyst is a microorganism which is capable of a selective oxidation of the sulfur in the organic sulfur compound, to said chemical compound, without concomitant oxidation of other components in combination with the organic sulfur compound.

11. The process of claim 4 wherein said microorganism is selected from the group consisting of Rhodococcus strain ATCC 55309 Rhodococcus strain ATCC 55310, *Rhodococcus rhodochrous* strain ATCC 53968, *Bacillus sphaericus* strain ATCC 53969, *Rhodococcus erythropolis* strain N1-36, *Rhodococcus erythropolis* strain D-1, Corynebacterium strain SY1, Brevibacterium strain DO and combinations thereof.

12. The process of claim 2 wherein said biocatalyst is prepared by cloning gene(s) encoding enzyme(s) responsible for selective oxidation of sulfur.

13. The process of claim 2 wherein said biocatalyst is prepared as purified or crude preparations of enzymes responsible for sulfur oxidation, and said purified or crude preparations are used directly in the form of free enzymes.

14. The process of claim 2 wherein said biocatalyst is prepared as purified or crude preparations of enzymes taken from microorganisms capable of sulfur oxidation and said purified or crude preparations are immobilized in gels or solid supports.

15. The process of claim 2 wherein said biocatalyst is prepared as purified or crude preparations of enzymes taken from microorganisms capable of sulfur oxidation, and said purified or crude preparations are modified with chemical groups to alter their solubility characteristics, to make them soluble in a hydrocarbon phase to allow more efficient contacting with the hydrocarbon phase.

* * * * *